(12) United States Patent  
Hoernig

(10) Patent No.: US 8,406,855 B2  
(45) Date of Patent: Mar. 26, 2013

(54) COMPUTER-OPERATED MAMMOGRAPHY SYSTEM WITH A CONTRAST AGENT INJECTOR, AND CONTROLLER AND OPERATING METHOD THEREFOR

(75) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/222,309

(22) Filed: Aug. 31, 2011

(65) Prior Publication Data

US 2012/0053456 A1 Mar. 1, 2012

(30) Foreign Application Priority Data

Aug. 31, 2010 (DE) .......................... 10 2010 035 926

(51) Int. Cl.
*A61B 6/00* (2006.01)
*A61B 5/05* (2006.01)
*A61B 6/04* (2006.01)
*G06K 9/00* (2006.01)

(52) U.S. Cl. ........... 600/431; 600/425; 382/131; 378/37

(58) Field of Classification Search .................. 600/425, 600/427, 431; 382/131; 378/37
See application file for complete search history.

(56) References Cited

U.S. PATENT DOCUMENTS

2006/0224066 A1 10/2006 Niethammer

FOREIGN PATENT DOCUMENTS

DE 10 2004 052 614 B3 10/2004

*Primary Examiner* — Michael Rozanski
(74) *Attorney, Agent, or Firm* — Schiff Hardin LLP

(57) ABSTRACT

A controller for a contrast agent-based, dual energy or two-spectrum tomosynthesis, has a control module that is designed for synchronized control of an injector and the mammography system. The control is based on measured, patient-specific values.

21 Claims, 2 Drawing Sheets

COMPUTER-OPERATED MAMMOGRAPHY SYSTEM WITH A CONTRAST AGENT INJECTOR, AND CONTROLLER AND OPERATING METHOD THEREFOR

BACKGROUND OF THE INVENTION

1. Field of the Invention

The present invention concerns contrast agent injection-based mammography systems and their mode of operation.

2. Description of the Prior Art

Digital contrast agent mammography ("contrast enhanced digital mammography", CEDM) is a technology with different characteristics in which—in contrast to conventional mammography—image data of a positionally fixed (normally compressed) breast can be acquired from different angles, which image data can later be reconstructed into a set of thin slice image exposures at high resolution. Compared to conventional x-ray mammography, tomosynthesis has a number of advantages; in particular, pathological structures can be detected more easily since interference signals due to superimposed tissue portions and artifacts can be reduced.

An iodine-containing contrast agent is normally used in digital full-field mammography. In a typical workflow for contrast agent-assisted digital mammography, initially a first (native) digital mammography exposure is acquired (preferably in two orthogonal planes: cranio-caudal/CC projection, mediolateral-oblique/MLO projection) in order to subsequently inject a contrast agent. Additional contrast agent exposures are subsequently produced as a reference. For this purpose it is essential that the subject (thus the breast) to be examined is located in a stationary position and does not move.

In dual energy tomosynthesis, the second exposure, or the second set of exposures, is executed with a spectrum at different energy than the first native blank exposure. A low-energy excitation typically takes place in the first exposure while a high-energy exposure for the tomoscan is provided for the second exposure. In the presentation of the acquired images the presentation of the glandular tissue (as is otherwise typical in mammography) occurs in the background, and the presentation of the contrast agent and of the contrast agent course in the breast takes higher priority.

In principle, two basic possibilities are provided for the implementation of a contrast agent mammography:

1. digital dynamic subtraction mammography, in which the one first, native blank exposure of the breast is compared with a second, contrast agent-enhanced reference exposure, and 2. dual energy subtraction mammography, in which two exposures with differing energy level are acquired after application of a (normally iodine-containing) contrast agent. The contrast agent enhancement can be depicted based on the different absorption properties arising from this and after logarithmic subtraction of the two exposures.

In the known methods for tomosynthesis (as described above), the contrast agent must initially be dosed and then must also be injected at an optimal point in time. In particular, the contrast agent may not be applied too early, and least of all in what is known as the wash-out phase. Furthermore, the contrast agent must also be dosed correctly. In conventional methods according to the prior art, a problem exists in practice because the dosing of the contrast agent is based only on an "on the spot" manual estimation by the treating physician and thus is frequently underdosed or overdosed. Patient-specific and automatic adaptation of the parameters to be controlled to the execution of the tomosynthesis has disadvantageously not been available in methods from the prior art. An additional problem is also that the point in time of the second exposure (tomoscan) must optimally be done according to the case-specific variables. If the second exposure is executed too early or too late, a sufficient result quality cannot be ensured. This in turn leads to the disadvantage that it, if it is needed, an additional system pass (associated with an increased radiation exposure to the patient) must be implemented again. In order to achieve an optimal significance and image quality, it is necessary to set different parameters for the execution of the tomosynthesis (in particular the dual energy tomosynthesis) in order to control the tomosynthesis process. Parameters include, for example, the contrast agent dosing, the point in time of the contrast agent application, the point in time of the execution of the second tomoscan, the determination of the point in time, and the degree of compression and decompression of the breast. A significant disadvantage of the systems known in the prior art is that a time-controlled and patient-specific control of the tomosynthesis is not possible. Moreover, there is no ability to implement the injector for the injection of the contrast agent and the mammography system synchronously based on the previously detected, patient-specific values.

SUMMARY OF THE INVENTION

An object of the present invention is to avoid the aforementioned disadvantages and to provide a time-controlled and patient-specific control of the injector and the mammography system.

In the following, the invention is explained in detail in connection with the computer-assisted medical system. Advantages, features and alternative embodiments are also applicable to other forms, in particular to the control module and the control method as well as the computer-readable storage medium and vice versa. Exemplary embodiments and alternatives that are described in connection with the system in the following thus need not be described again for the method, control module, and storage medium.

A basis of the present invention is that patient-specific values are detected and are to be supplied to a control module in order to automatically calculate injection-specific data. The calculated, injection-specific data are then relayed to the injector in order to control the injection with such data. However, the measured (or otherwise registered) patient-specific values and the injection-specific data are also still of relevance to other processes within the scope of mammography. Therefore the control module according to the present invention takes these values and data into account in order to control the compression or decompression of the subject to be examined (the breast) at the mammography apparatus. Furthermore, these values and data are taken into account in the control and execution of the second tomoscan; in particular, depending on the patient-specific values and the injection-specific data a point in time is determined as to when the second tomoscan should be executed, and at what energy level. A significant advantage is that the mammography can be adapted to the respective patient and to the injection of the contrast agent that has taken place. This can in turn lead to savings of contrast agent and to a lower contrast agent exposure, and overall contributes to the improvement of the mammography process.

The control module is thus characterized by the calculation of three different categories of data or values:

1. injection-specific data for the control of the injector, comprising type of contrast agent, dosing and speed;

2. compression data to control the mammography apparatus to compress and/or decompress the breast, comprising point in time, duration and degree;

3. mammography apparatus-related data for the control of the mammography apparatus given the execution of the tomoscan, comprising: start point in time, a kilovolt range (energy level).

It is essential that all control data that are calculated by the control module are calibrated to one another, independently of when the individual actions are executed. In the event that an action should not be executed, this data set is accordingly not taken into account in the activation of the subsequent actions. For example, it may be the case that the compression is not implemented at all, or only after a second tomoscan and before a third tomoscan.

Two aspects are important to the invention. First, it enables a synchronized control of injection, compression/decompression and mammography. "Synchronized" includes a temporal aspect and an aspect with regard to content. "Temporal" means that the start point in time for the execution of the actions (compression, decompression, exposure/second tomoscan) is adapted to the other patient-specific and case-specific conditions. "With regard to content" means that parameters for the adjustment or configuration of the mammography apparatus are adapted to the patient-specific and case-specific (and also the injection-specific) conditions. It can thus be ensured that the second tomoscan is executed at the correct point in time with the correct energy level in relation to the respective patient and the injection of the contrast agent (which contrast agent, how much, how quickly it is applied, which patient-specific values exists, such as breast size, tissue structure, etc.).

Secondly, a monitoring mechanism is provided that is geared toward the application of the contrast agent. The monitoring mechanism should ensure that the mammography apparatus is geared towards the contrast agent or, respectively, is calibrated with this for the execution of at least the second tomoscan. A warning can be emitted when an inconsistency with a desired reference data set is established. The desired reference data set can be provided in advance in a data structure and provides specific, reliable associations of contrast agent settings (type of contrast agent, dosing, feed speed etc.) and apparatus control parameters (point in time of the execution, energy level etc.). The establishment of an inconsistency can be executed either manually (by the user manually entering and testing which contrast agent is actually located in the injector at the time) or automatically (by labeling the contrast agent cannula with an RFID signature uniquely identifying it, or by labeling the injector with an RFID signature, wherein a determined injector is respectively provided for application of a specific contrast agent). With the monitoring mechanism it should be ensured that, for example, iodine-containing contrast agent is always used and that this can also be shown by the system. It should be prevented that, for example, gadolinium-containing contrast agent (Gadovist, for example) is accidentally used whose absorption edge (at 50 keV) is markedly higher than that of iodine (33 keV). The high-energy scan would then not be able to image the contrast agent, which overall would lead to an unnecessary contrast agent exposure. Given the use of Gadovist, the system would have to be operated at a higher energy in order to be able to image gadolinium. Naturally, it is also possible that the contrast agent is not adapted to the tomoscan but rather that the tomoscan is adapted to the contrast agent. The mammography apparatus thus can be operated in a corresponding energy mode for the high-energy tomoscan depending on the contrast agent that is used.

To achieve the aforementioned object, the present invention includes (among other things) a computer-assisted medical system that has a mammography apparatus and an injector to inject contrast agent within the scope of a mammogram, wherein the mammogram provides a first and at least one second tomoscan.

The invention is characterized by the provision of a control module that is designed for synchronized (in terms of time and content) control of the injector and the mammography apparatus, wherein the control module measures (or imports) values for predefinable, patient-specific parameters that serve as a basis for automatic calculation of a contrast agent quantity and a contrast agent flow speed. The calculated contrast agent-related data (this term is also used synonymously with the term "injection-specific data" in the following) are relayed to the injector for execution of the injection. The control module is furthermore designed in order to automatically determine compression data (degree, point in time, duration etc.) for the compression and decompression of the examination subject based on the patient-specific values and based on the injection-specific data. Furthermore, the control module is designed in order to control the (at least one) second tomoscan depending on patient-specific values, injection-specific data and compression data. In particular, an energy excitation level and a start point should be calculated with which the (at least one) second tomoscan should be executed. The calculation of the start point advantageously takes place based on patient-specific data. These can be the already-acquired values, or the calculation can be indirectly based on the acquired values and use the calculated contrast agent-specific or injection-specific data. Other or additional patient-individual values can also be taken into account. The calculated mammography apparatus-related data are relayed to the mammography apparatus for control.

A computer-based system for use in a clinical medical environment typically includes a mammography system or a mammography apparatus, an injector to inject contrast agent within the scope of the mammogram, and a computer-based control module. Moreover, in alternative embodiments the system can include additional computer-based modules and interfaces to a medical administration system, for example a PACS (Picture Archiving and Communication System), an RIS (Radiology Information System) or additional systems.

The mammography apparatus can be a mammography system known in the prior art, with an x-ray source, a detector and a compression mechanism to compress the breast. In the preferred embodiment, the mammography apparatus is fashioned to execute a digital full-field mammogram that can be applied in different embodiment variants, for example a dual energy tomosynthesis, a two-spectra tomosynthesis or a temporal subtraction tomosynthesis (temporal subtraction technique), or combinations of the aforementioned techniques as well.

According to a preferred embodiment of the present invention, the mammography has at least two mammography exposures, namely a native first blank exposure and a second mammography exposure that are respectively also designated as a tomoscan. The second acquisition is advantageously executed after the application of the contrast agent in order to be able to show the contrast agent course. In embodiments, more than one second mammography acquisition can be provided whose start point is then likewise to be determined by the control module. In a simple embodiment, the second tomoscan can also be omitted so that only a mammography exposure (tomoscan) is produced. The control module accordingly does not need to determine the start point for the second tomoscan; rather, in this case the control module would merely be designed to control the injector.

As mentioned, the mammography procedure is advantageously a contrast agent-based mammography procedure. However, this is not absolute necessary for the execution of the invention. It can also be that no contrast agent should be injected in the tomosynthesis. Then the control module is merely fashioned in order to control the compression process at the mammography apparatus and furthermore in order to calculate and trigger the start point for the additional tomoscan. In this case the control of the injector can be omitted.

In the preferred embodiment, the first tomoscan takes place with a low energy level and before the contrast agent injection while the second tomoscan is already executed as a high-energy scan after contrast agent is injected. The contrast agent is advantageously iodine or an iodine-containing substance.

The injector is an apparatus to inject the contrast agent within the scope of a mammography examination and can be integrated into the mammography apparatus or be provided as a separate device. According to one primary application, only one injection is implemented. However, other applications require a repeated injection of contrast agent. The invention then provides that the control module determines and controls the point in time and the contrast agent dose as well as the injection speed for all injections to be implemented. The injector includes a communication interface for data transfer with the mammography apparatus and with the control module. Moreover, additional interfaces with medical administration systems (PACS, RIS etc.) can be provided. One important aspect of the invention is also that a synchronized control of injection and mammography or exposure is executed. In other words, it should be ensured that the mammography is adapted to the administration of the respective contrast agent and, for example, the incorrect energy level or a point in time that is determined to be too early or late (in which the applied contrast agent has no effect or a poor effect) are not selected in or for the execution of the second tomoscan.

The control module is designed to be hardware-based and/or software-based and can be fashioned as a separate instance (for example on the server that is connected with the mammography apparatus and the injector with regard to data), or it can be provided at the mammogram, for example in the form of a separate application. Moreover, it is possible to fashion the control module as a distributed system, wherein portions of the module are provided on the mammography apparatus and other parts are provided at a different computer-based instance (a server, for example). In alternative embodiments, portions or components of the control module can also be provided at the injector. All components or portions of the control module are connected in terms of data. Moreover, the control module interacts with the mammography apparatus and the injector to control them.

The control module has an input interface to record data. Which data the control module should record can be configured in advance. Here parameters are specified that are used for the control of the injector and the mammography apparatus according to the invention. In particular, the following parameters are taken into account:
  weight of the patient
  fat proportion of the body
  body fat
  height of the patient
  body mass index and
  additional patient-specific parameters.

It is also possible to derive individual values from other parameters. For example, the body mass index can be derived from the weight and the height of the patient and the breast can be derived from the weight and the fat proportion. Moreover, additional parameters can be configured. Typically the values regarding the predefined parameters are measured immediately before the mammography acquisition. This has the advantage of ensuring that current values and no obsolete data (for example given a weight change) are always used in the determination of the contrast agent. As an alternative to this, it is possible to import already acquired values about an interface. This has the advantage that already acquired exposures can be resorted to given repeated mammography acquisitions. There are two variants again for the measurement of the values: on the one hand, the values can be measured at separate devices (scales etc., for example) and then be imported manually via a user interface or automatically via a data connection. It is possible that the devices in order to measure the values are already integrated into the mammography apparatus.

The control module includes a calculation module that calculates contrast agent-related data from the acquired values without additional user interactions being necessary. The contrast agent-related data are in particular the contrast agent dosing and a determination of the flow speed with which the contrast agent is injected (what is known as the injection speed, measured in ml/sec). More complex embodiments can calculate additional data here in relation to the contrast agent.

In a preferred embodiment, the automatically calculated, contrast agent-related data are relayed to the injector to control the injection without additional user inputs. Alternatively, the calculated data can be presented again at an interface in order to enable a check by the user. The user must then input a confirmation signal that identifies that the user is in agreement with the calculated injection data. An additional monitoring is provided by checking whether the calculated injection data also agree with the variables present in the injector. For example, it can be checked (manually or automatically by means of RFID technology) whether the correct contrast agent is also actually provided in the injector. In the event that it is not, a warning signal (acoustic or optic) is output. The injection is only started if the check could be concluded successfully. The injection is thereupon executed with the calculated data. Otherwise, in the event that the user thus does not input a confirmation signal either manual determination of the contrast agent-related data is queried or the process can be terminated. It is therefore also possible that the user modifies the automatically calculated contrast agent information.

The injector is thereupon controlled with the calculated injection data.

Depending on the application of the mammography system it is provided that the subject to be examined (thus the breast) is compressed and decompressed in order to be able to ensure a position fixing of said breast during the mammography exposure. The degree or the strength of the compression can likewise be adjusted. This takes place at the mammography apparatus. The control module is therefore designed in order to automatically calculate compression data from the measured or, respectively, acquired values (and possibly from the injection-specific data), which compression data are then forwarded to the mammography apparatus to control the compression and decompression.

Moreover, the control module is designed to calculate a start point from the measured patient-specific values, at which start point and with what energy level a second or an additional tomoscan should be implemented. However, this is only reasonable in the event that it is an application in which multiple mammography exposures are produced (for example a dual-energy tomosynthesis). This aspect represents a marked advantage relative to the systems known from the prior art since the point in time for the second (or the additional) tomoscan also directly affects the image quality of the acquired exposures. Namely, if the second tomoscan is executed too early or too late, a sufficient image quality is no longer present. The image quality can therefore be optimized via the automated adjustment and control of the mammography apparatus.

An additional important aspect is apparent in that the data calculated by the control module (said data comprising: contrast agent dose, contrast agent flow speed, compression/decompression data and settings of the mammography apparatus such as energy level and point in time for the additional tomoscan etc.) are adapted to the patient data sets or, respectively, linked with these. The calculated values can then be retrieved for additional examinations via the patient data and do not need to be recalculated again. This represents a performance advantage and leads to the situation that errors due to incorrect manual inputs can be avoided. Moreover, the calculated and derived data can be used for additional and repeat applications.

An additional important effect is apparent in that a common controller is provided for mammography apparatus and injector. The mammography apparatus can therefore be activated together with the injector in a synchronized manner. The image sequences acquired by the mammography apparatus are consequently synchronized (in terms of time [sic]) with the contrast agent curves so that, for a diagnosis, to which point in time after the contrast agent injection the acquired image data are related is recognizable at any point in time. The term "contrast agent curves" here means all graphical or other representations of the examination subject with the injected contrast agent and its course, in particular intensity curves that characterize an enrichment of the contrast agent per unit of time.

The control of the mammography apparatus with regard to the execution of the compression/decompression and the execution of the exposure is thus coupled with the control and execution of the injection or, respectively, with the injector. It can thus be ensured that, for example, the second tomoscan is also executed at the correct point in time and with the correct energy, depending on the injection and/or the compression/decompression.

Since the invention provides different series for execution of the steps, a different sequence of method steps can also be provided and, for example, a repeated injection and an additional tomoscan can be necessary after the second tomoscan. It is significant that all actions or steps to be executed at the injector and at the mammography apparatus (for compression/decompression and for the actual exposure) are matched to one another.

One advantage of the achievement according to the invention is also apparent in that, in addition to the patient-specific control of the contrast agent injection and the tomosynthesis (in particular with regard to the chronological workflow of the same), a patient-individual control of the compression and decompression procedures is also possible. Moreover, it is no longer required to control two independent systems as before (the mammography system and the injector system); rather, according to the invention a synchronized control of the injector together with the mammography system can be executed with one device (here the control module).

According to one aspect of the invention, the data transfer between the individual elements of the computer-assisted system takes place wirelessly or via wires, in particular via radio or via another wireless network connection (for example WLAN or Bluetooth). The communication between the control module, the injector and the mammography apparatus advantageously takes place wirelessly.

In a preferred embodiment, the mammography apparatus is operated as a master and the injector is operated as a slave.

As already mentioned, data calculated at the control module can again be confirmed at by the user via a user interface in order to then be relayed to the injector and the mammography apparatus for control. The calculated data are typically stored in the system for later follow-up applications. The data are advantageously linked with the patient data. It is therefore possible to present the acquired image sequences together with the contrast agent curves on a display.

The above object is also achieved by a control module that can be used for a medical system (as described above).

The above object also is achieved by a control method for a contrast agent-based mammography apparatus with an injector to inject the contrast agent. Values for pre-configured, patient-specific parameters are thereby measured, input or imported in a first step. Contrast agent-specific data (in particular dosing and flow speed) are then calculated from the measured values, wherein the contrast agent-related values are relayed to the injector for execution of the injection. In a further step, a start point is determined for the execution of one or more additional tomoscans. This point in time is then relayed to the mammography apparatus in order to activate the same to initiate the additional tomoscans.

In an embodiment of the method, the control method can furthermore be fashioned to control the compression/decompression procedure during the mammography acquisitions. This can likewise take place based on the measured patient-specific values, in particular a breast thickness and a tissue composition and possibly additional values. These compression-related data are likewise relayed to the mammography apparatus to control the compression/decompression.

In principle, two embodiments are provided to control the mammography apparatus. It is possible to initially acquire all values that the control module requires to calculate the data. After calculation of the data, the mammography apparatus-related data that are necessary to control the further mammography workflow are collectively relayed to the mammography apparatus for control. It is also possible to provide a sequential procedure here and to only calculate the required data to control the mammography apparatus in the respective phase just before the beginning of said phase, and to relay said required data to the mammography apparatus. In this case the control data are transmitted in stages and separately from one another. This has the advantage that the control data exist in a respective current form and the calculations can be executed independent of one another.

DESCRIPTION OF THE PREFERRED EMBODIMENTS

In the following, the basic design of the system according to the invention is described in detail in connection with FIG. 1. A mammography apparatus M is fashioned to execute a contrast agent-based dual energy tomosynthesis. For this an injector I is connected to the system. The system moreover includes a computer at which a control module S can be executed and/or operated, wherein the control module S is designed for synchronized control of the mammography apparatus M and the injector K. Either the control module S can be installed on the computer as software and be executed there in the form of an application with a user interface, or it can be integrated into the computer as a hardware module (for example as a microprocessor module), wherein the hardware or, respectively, the microprocessor has the functionality of the control module S described in detail in the following. In a preferred embodiment, a server or a database to store the mammography-relevant data and the data calculated by the control module S is additionally provided at the system.

Figure 1:
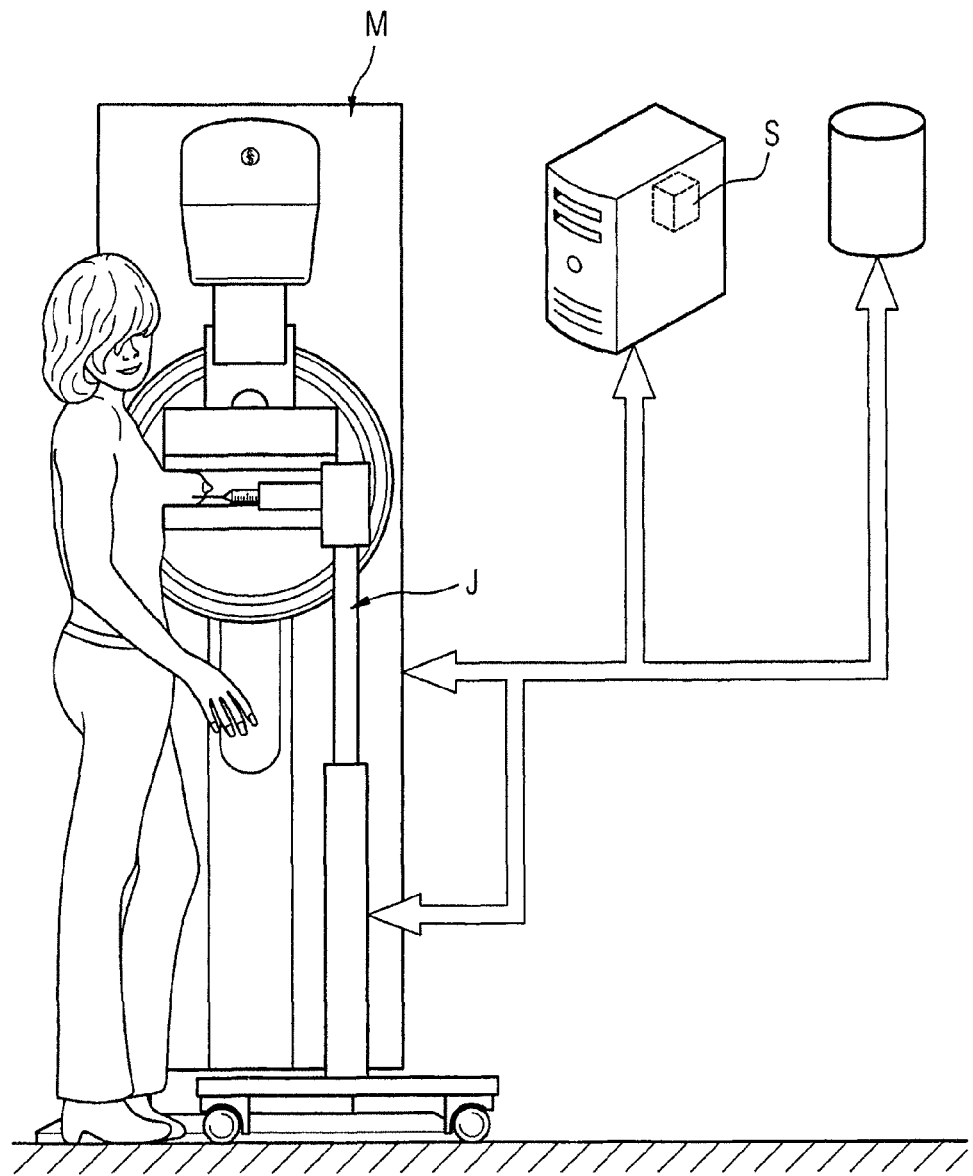
FIG. 1 is a schematic overview of a mammography apparatus, an injector and a control module according to the invention according to a preferred embodiment.

The embodiment presented in FIG. 1 refers to the situation that the control module S is completely fashioned on a central control computer. Alternatively, portions of the control module S can also be fashioned at the mammography apparatus M and/or the injector I or another instance. The control module S can have a user interface for input and to confirm data.

In dual energy tomosynthesis it is provided that two tomoscans are executed, of which the first is executed with low energy and the second is executed with high energy. The point in time for the initialization of the second tomoscan is dependent on patient-specific values. These are advantageously calculated automatically by the control module S after the patient-specific values have been measured or imported by the control module S.

In contrast agent-based tomosynthesis it is necessary that a contrast agent injection is conducted before a tomoscan so that the contrast agent enhancement with the contrast agent kinetics in the lesion area can be visibly shown in the following exposure. Before execution of the injection, the dosing of the contrast agent and the feed speed must therefore be set. According to the invention, this is controlled via the control module S based on the patient-specific values. For this the control module S is connected with the injector I via a wireless system (WLAN or Bluetooth etc.), for example. After the automatic determination of the contrast agent-related data, these are forwarded to the injector to control the injection. In a preferred variant of the invention, the control module S additionally has a user interface at which the calculated data of the control module are displayed. This has the advantage that the user can again confirm the automatically calculated data for injection control and mammography control again via a confirmation signal before these are relayed to the injector and/or to the mammography apparatus.

According to a preferred embodiment, the first tomoscan is implemented in the same examination as the second tomoscan or subsequent tomoscans. This has the advantage that a position-conforming fixing of the examination subject can be ensured and no additional referencing measures of acquired image data sets are necessary. In one variant of the invention it is possible that a first tomoscan already exists because it has been acquired at an earlier point in time. A registration procedure must then be implemented in order to make the first tomoscan comparable with the second tomoscan to be acquired.

Figure 2:
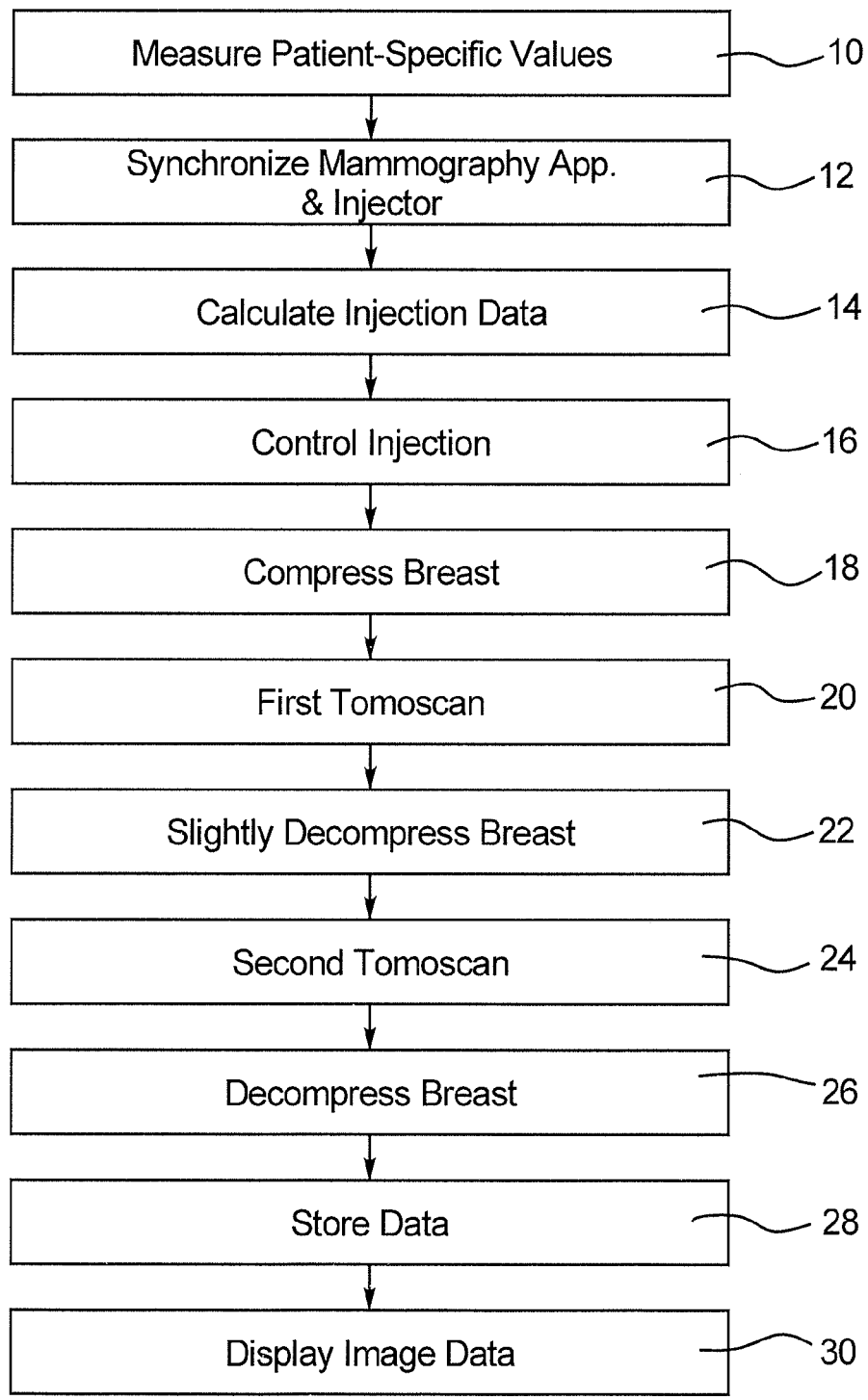
FIG. 2 is a flowchart of an embodiment of the method of the present invention.

In the following an exemplary workflow according to a preferred embodiment of the invention is shown in connection with FIG. 2.

In a first Step 10, patient-specific values are measured. It is thereby provided that which values the control module S should record for the patient-specific parameters is determined in a configuration phase.

In the next step 12, synchronization between the mammography apparatus M and the injector 1 is implemented.

In Step 14, injection data are calculated that are relayed to the injector I to control the injection.

In Step 16 the injection is executed with the calculated injection data.

A compression of the breast can be executed in Step 18.

A first tomoscan is executed in the subsequent Step 20. Here it is noted that alternative embodiments also provide a different point in time for the execution of the first tomoscan.

A slight decompression of the breast can be executed in Step 22.

The second tomoscan can be executed in Step 24. However, before execution of the second tomoscan the control module S can have calculated the compression-specific data and relayed it to the mammography apparatus M. The compression-specific data also comprise information as to when a compression should be executed, when a decompression should be executed and additional cycles of compression/decompression. Furthermore, the control module S must already have relayed the mammography-specific data to the mammography apparatus M before execution of the second tomoscan. In particular, this is thereby the starting point for the triggering of the second tomoscan.

A decompression of the breast is executed at Step 26.

A storage of the data, in particular the calculated data in connection with the acquired data, can be executed in Step 28.

In the last Step 30 the image data can be shown on a monitor together with the contrast agent curves.

Additional embodiments provide a different sequence of steps. For example, cycles of compression/decompression can be designed differently, or occur at different points in time. Moreover, it is also possible to have already executed the first tomoscan at an earlier point in time.

Although modifications and changes may be suggested by those skilled in the art, it is the intention of the inventor to embody within the patent warranted hereon all changes and modifications as reasonably and properly come within the scope of his contribution to the art.

I claim:

1. A medical system comprising:

a mammography apparatus configured to obtain tomographic scans of a breast of a patient in a mammography procedure, said tomographic scans including a first tomoscan and at least one second tomoscan following said first tomoscan;

said mammography apparatus comprising a movable compression plate operable to selectively compress and decompress the breast in the mammography apparatus during said mammography procedure;

a contrast agent injector configured to interact with the patient to inject contrast agent into the patient;

a computerized control unit configured to operate said mammography apparatus, including operating said compression plate, and to operate said contrast agent injector with synchronized control of operation of said contrast agent injector and said mammography apparatus;

said control unit having an input provided with predefined, patient-specific parameters having respective values that are specific to the patient;

said control unit being configured to automatically calculate injection-specific data, comprising a contrast agent quantity and a contrast agent flow speed, from said patient-specific parameters, and to control injection of said contrast agent into the patient via said contrast agent injector using said injection-specific data;

said control unit also being configured to automatically determine compression data dependent on said injection-specific data, and to control compression and decompression of the breast in the mammography apparatus by moving said compression plate dependent on said compression data; and said control unit also being configured to calculate mammography apparatus control data dependent on said patient-specific parameters, said injection-specific data and said compression data, and to control said mammography apparatus dependent on said mammography apparatus control data, said mammography apparatus control data including at least a designation of a starting point in time for said at least one second tomoscan, with said mammography apparatus control data and said compression data and said injection-specific data being matched to each other.

2. A system as claimed in claim 1 wherein said control unit is integrated into said mammography apparatus.

3. A system as claimed in claim 1 wherein said control unit is located at a remote location with respect to a site of said mammography apparatus, and wherein said medical system comprises a communication link configured for data exchange between said control unit and said mammography apparatus.

4. A system as claimed in claim 1 wherein said control unit is configured by hardware to calculate said injection-specific data, said compression data, and said mammography apparatus control data.

5. A system as claimed in claim 1 wherein said control unit is configured by software to calculate said injection-specific data, said compression data, and said mammography apparatus control data.

6. A medical system as claimed in claim 1 comprising a data communication link between said control unit and said contrast agent injector, selected from the group consisting of hardwired links and wireless links.

7. A medical system as claimed in claim 1 wherein said mammography apparatus and said contrast agent injector are configured to be controlled synchronously from said control unit, with said mammography apparatus configured as a master and said contrast agent injector configured as a slave.

8. A medical system as claimed in claim 1 wherein said control unit comprises an interface configured to communicate with a data storage unit, and wherein said control unit is configured to store said injection-specific data, said compression data and said mammography apparatus control data in said data storage unit via said interface.

9. A medical system as claimed in claim 1 wherein said input to said control unit comprises an interface configured to import said patient-specific values into said control unit, and to import said first tomoscan, as an acquired data set, and configured to interface with an external unit consisting from the group consisting of a further processor and a memory.

10. A medical system as claimed in claim 9 wherein said control unit is configured to bring said first tomoscan into registration with said at least one second tomoscan.

11. A computerized control unit for a medical system comprising a mammography apparatus configured to obtain tomographic scans of a breast of a patient in a mammography procedure, said mammography apparatus comprising a movable compression plate operable to selectively compress and decompress the breast in the mammography apparatus during said mammography procedure, and said medical system further comprising a contrast agent injector configured to interact with the patient to inject contrast agent into the patient, said control unit comprising:

a processor configured to operate said mammography apparatus to implement a first tomoscan followed by at least one second tomoscan, including operating said compression plate, and to operate said contrast agent injector for synchronized control of operation of said contrast agent injector and said mammography apparatus;

said processor having an input provided with predefined, patient-specific parameters having respective values that are specific to the patient;

said processor being configured to automatically calculate injection-specific data, comprising a contrast agent quantity and a contrast agent flow speed, from said patient-specific parameters, and to emit said injection-specific data at a first output to control injection of said contrast agent into the patient via said contrast agent injector using said injection-specific data;

said processor also being configured to automatically determine compression data dependent on said injection-specific data, and to emit said compression data at a second output to control compression and decompression of the breast in the mammography apparatus by moving said compression plate dependent on said compression data; and said processor also being configured to calculate mammography apparatus control data dependent on said patient-specific parameters, said injection-specific data and said compression data, said mammography apparatus control data including at least a designation of a starting point in time for said at least one second tomoscan, with said mammography apparatus control data and said compression data and said injection-specific data being matched to each other, and to emit said mammography apparatus control data at a third output to control said mammography apparatus.

12. A method for operating system comprising a mammography apparatus and a contrast agent injector configured to interact with a patient to inject contrast agent into the patient said method comprising from a control unit operating said mammography apparatus to obtain tomographic scans of a breast of a patient in a mammography procedure, said tomographic scans including a first tomoscan and at least one second tomoscan following said first tomoscan, said mammography apparatus comprising a movable compression plate operable to selectively compress and decompress the breast in the mammography apparatus during said mammography procedure;

from said control unit, operating said mammography apparatus, including operating said compression plate, and operating said contrast agent injector with synchronized control of operation of said contrast agent injector and said mammography apparatus;

providing said control unit with predefined, patient-specific parameters having respective values that are specific to the patient;

in said control unit, automatically calculating injection-specific data, comprising a contrast agent quantity and a contrast agent flow speed, from said patient-specific parameters, and controlling injection of said contrast agent into the patient via said contrast agent injector using said injection-specific data;

in said control unit, also automatically determining compression data dependent on said injection-specific data, and controlling compression and decompression of the breast in the mammography apparatus by moving said compression plate dependent on said compression data; and in said control unit, also calculating mammography apparatus control data dependent on said patient-specific parameters, said injection-specific data and said compression data, said mammography apparatus control data including at least a designation of a starting point in time for said at least one second tomoscan, with said mammography apparatus control data and said compression data and said injection-specific data being matched to each other.

13. A method as claimed in claim 12 comprising integrating said control unit into said mammography apparatus.

14. A method as claimed in claim 12 comprising locating said control unit at a remote location with respect to a site of said mammography apparatus, and exchanging data via a communication link between said control unit and said mammography apparatus.

15. A method as claimed in claim 12 comprising configuring said control unit by hardware to calculate said injection-specific data, said compression data, and said mammography apparatus control data.

16. A method as claimed in claim 12 comprising configuring said control unit by software to calculate said injection-specific data, said compression data, and said mammography apparatus control data.

17. A method as claimed in claim 12 comprising exchanging data via a data communication link between said control unit and said contrast agent injector, selected from the group consisting of hardwired links and wireless links.

18. A method as claimed in claim 12 comprising configuring said mammography apparatus and said contrast agent injector to be controlled synchronously from said control unit, with said mammography apparatus configured as a master and said contrast agent injector configured as a slave.

19. A method as claimed in claim 12 comprising providing said control unit with an interface configured to communicate with a data storage unit and, from said control unit, storing said injection-specific data, said compression data and said mammography apparatus control data in said data storage unit via said interface.

20. A method as claimed in claim 12 comprising providing said control unit with an interface configured to import said patient-specific values into said control unit, and to import said first tomoscan, as an acquired data set, and configured to interface with an external unit consisting from the group consisting of a further processor and a memory.

21. A method as claimed in claim 20 comprising, in said control unit, bringing said first tomoscan into registration with said at least one second tomoscan.

* * * * *